United States Patent [19]
Eckert et al.

[11] Patent Number: 5,393,486
[45] Date of Patent: Feb. 28, 1995

[54] METHOD FOR MAKING ORTHODONTIC APPLIANCE HAVING TEXTURED BONDING SURFACE

[75] Inventors: Robert P. Eckert, Hinckley, Ohio; Evangelos G. Georgakis, Altaloma, Calif.

[73] Assignee: Minnesota Mining and Manufacturing Company, St. Paul, Minn.

[21] Appl. No.: 164,159

[22] Filed: Dec. 9, 1993

[51] Int. Cl.6 .................... B22F 5/00; B22C 7/02
[52] U.S. Cl. ........................... 419/66; 419/65; 419/36; 419/38; 164/246
[58] Field of Search ............. 419/36, 38, 69, 66; 249/54; 433/8, 9; 164/34, 246

[56] References Cited

U.S. PATENT DOCUMENTS

| D. 290,040 | 5/1987 | Kelly | D24/16 |
|---|---|---|---|
| 3,765,091 | 10/1973 | Northcutt | 433/9 |
| 4,068,379 | 1/1978 | Miller et al. | 433/9 |
| 4,100,678 | 7/1978 | Yatabe | 433/9 |
| 4,165,561 | 8/1979 | Miller et al. | 433/9 |
| 4,243,386 | 1/1981 | Kawaguchi | 433/9 |
| 4,322,206 | 3/1982 | Reynolds | 433/9 |
| 4,479,527 | 10/1984 | Boettcher | 164/34 |
| 4,531,566 | 7/1985 | Boettcher | 164/246 |
| 4,544,353 | 10/1985 | Maurer et al. | 433/9 |
| 4,626,209 | 12/1986 | Tsai et al. | 433/9 |
| 4,842,513 | 6/1989 | Haarmann | 433/9 |
| 4,936,773 | 6/1990 | Kawaguchi | 433/9 |
| 5,267,854 | 12/1993 | Schmitt | 433/8 |
| 5,318,440 | 6/1994 | Adam et al. | 433/8 |

OTHER PUBLICATIONS

Supreme TM Mini-Twin brochure, Ortho Organizers, Inc., copyright date unknown.

*Primary Examiner*—Donald P. Walsh
*Assistant Examiner*—John N. Greaves
*Attorney, Agent, or Firm*—Gary L. Griswold; Walter N. Kirn; James D. Christoff

[57] ABSTRACT

A method of making an orthodontic appliance such as a bracket includes the step of forming a preform of molding material while a portion of the molding material is in contact with a textured portion of a web. The web is subsequently degraded by a thermal or solvent degrading process to leave a witness impression on the underside of the preform. The web optionally serves as a conveyor to move the preform from one processing area to another, and optionally has the appearance of a woven material such that the resulting appliance resembles a mesh base appliance having undercut regions.

17 Claims, 3 Drawing Sheets

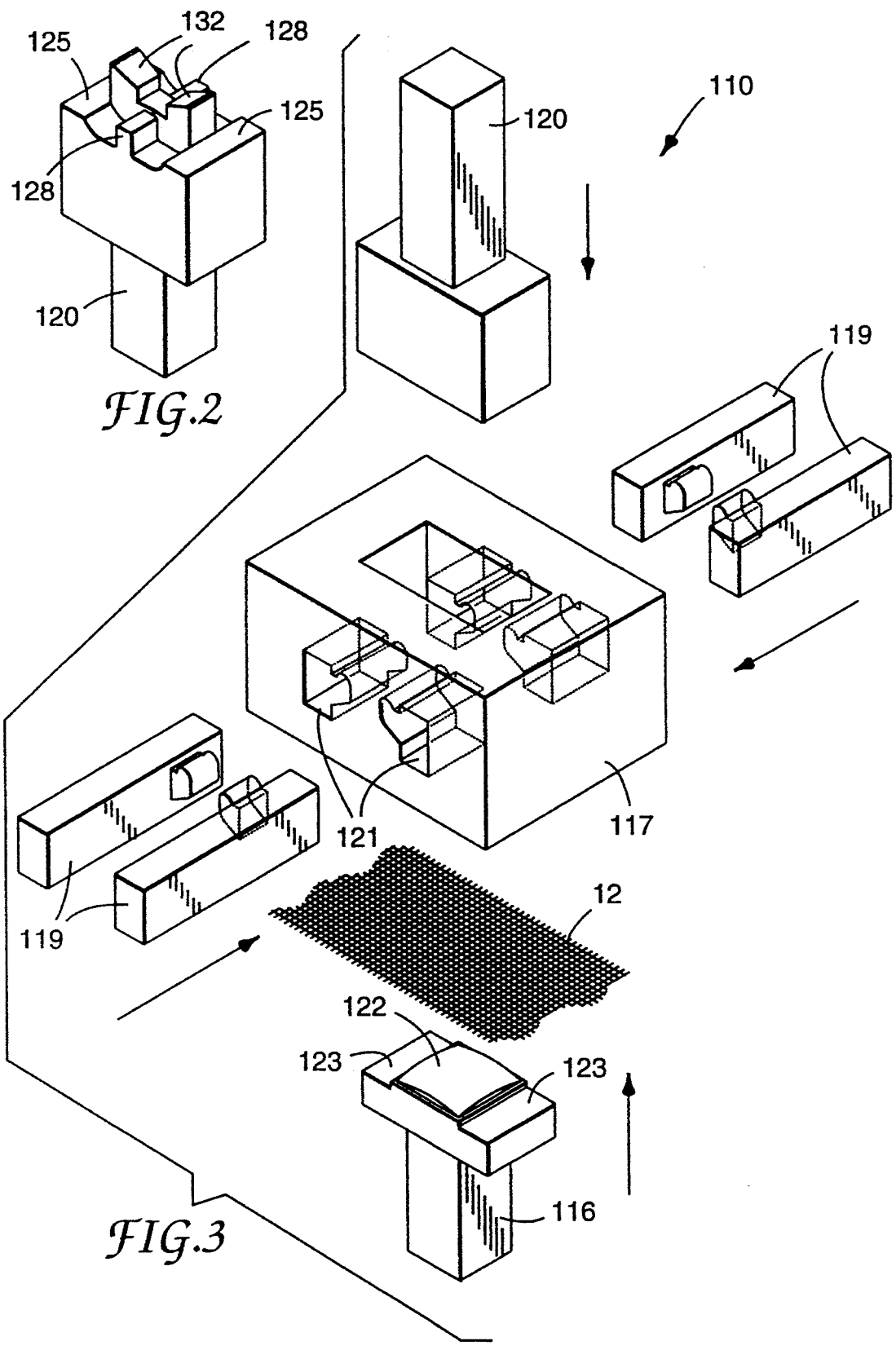

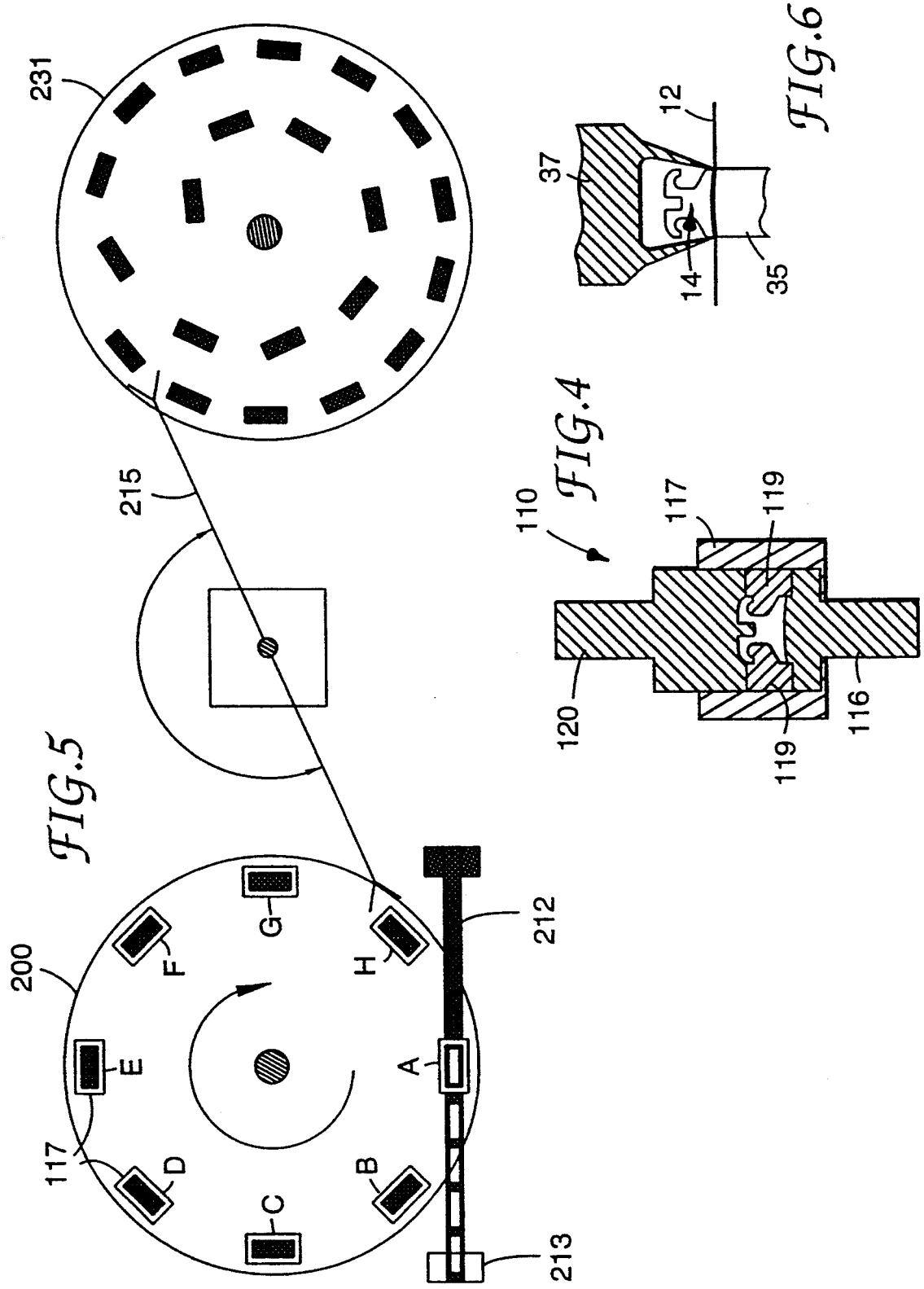

METHOD FOR MAKING ORTHODONTIC APPLIANCE HAVING TEXTURED BONDING SURFACE

BACKGROUND OF THE INVENTION

1. Field of the Invention

This invention relates to a method of making orthodontic appliances such as brackets having a textured surface for bonding the appliance to a tooth.

2. Description of the Related Art

Orthodontic treatment concerns movement of malpositioned teeth to orthodontically correct positions. During treatment, tiny orthodontic appliances known as brackets are connected to anterior, cuspid and bicuspid teeth, and an archwire is placed in a slot of the brackets. The archwire forms a track to guide movement of the teeth to desired positions for orthodontically correct occlusion. Typically, the ends of the archwire are held by appliances known as buccal tubes that are secured to molar teeth.

In previous years, orthodontic appliances such as brackets and buccal tubes were connected to teeth by welding or brazing each appliance to a band that was then placed over the desired tooth in encircling relation. In more recent years, however, it has become common practice to bond orthodontic brackets directly to the surface of the tooth. Omission of the metal bands associated with the brackets provides a more aesthetic appearance than brackets welded to bands, and helps alleviate the problem of the "metallic mouth" appearance that is often associated with orthodontic treatment.

Occasionally, brackets that are directly bonded to teeth may unintentionally debond from the surface of the teeth before treatment is completed. In some cases, bond failure is due to relatively large forces imposed on the bracket, as when the patient bites into a relatively hard food item or is unintentionally bumped in the mouth by an external object. In other instances, a bracket may debond from excessive force exerted by the archwire, such as when the orthodontist places a relatively sharp bend or twist in the archwire in an attempt to urge teeth toward desired positions. Bond failure may also be due to the use of an inadequate amount of adhesive, or due to the use of an improperly selected or improperly cured adhesive.

Premature debonding of orthodontic brackets represents a nuisance to both the orthodontist and the patient. If debonding occurs outside of the orthodontist's office, the patient must return to the office where the archwire is removed from all of the brackets and the surface of the tooth lacking the bracket is then cleaned in preparation for rebonding. Unless the debonded bracket can be cleaned of old adhesive and reused, a new bracket is selected for attachment. Next, the bracket is precisely positioned on the tooth and the adhesive is cured, following which the archwire is replaced in the bracket slots and ligated in place. As can be appreciated, such a procedure is time consuming and increases the expense and effort associated with orthodontic treatment.

The phenomena of bond failure between orthodontic brackets and the surfaces of associated teeth may arise at the location of the interface between the base of the bracket and the adhesive, in the adhesive itself, or at the interface between the adhesive and the tooth surface. Bond failures that occur between the adhesive and the base of orthodontic brackets are of particular concern to the manufacturers of brackets, and many attempts have been made over the years to improve the base of the bracket to enhance the bond of the bracket to the adhesive.

U.S. Pat. No. 4,068,379 illustrates an orthodontic bracket having a bonding base made of an initially separate mesh material that resembles a small wire screen. As the bracket is pushed into adhesive during bracket placement, the adhesive flows in and around openings of the mesh and mechanically interlocks with the mesh once the adhesive has cured. However, the mesh base is considered a significant factor in the manufacturing expense of orthodontic brackets, since such a manufacturing process often entails carefully cutting the mesh to shape, aligning the mesh with the bracket body, and then brazing the mesh to fix the mesh to the bracket body.

U.S. Pat. No. 290,040, assigned to the assignee of the present invention, illustrates an orthodontic bracket having an integral machined bonding base with substantial surface area and undercut regions for contact with the adhesive. U.S. Pat. No. 340,523, also assigned to the assignee of the present invention, illustrates an orthodontic bracket that is made of a sintered metal powder material, wherein a series of posts formed in the base during a metal injection molding operation are slightly peened over during a subsequent tumbling operation to provide a series of undercut regions.

Many orthodontists favor brackets having a base with increased surface area for bonding, and often prefer a base having a mesh pad, peened over posts or other structure that provides undercut regions, since such undercut regions provide protruding structure that hinders the adhesive from detaching from the bracket once the adhesive cures to a hardened condition. Consequently, as manufacturers search for new methods of making orthodontic appliances, increased attention has been directed toward discovering an improved method of making an orthodontic appliance that has a textured or nonsmooth bonding surface, and especially a method that provides the appliance with a bonding surface having undercut regions.

SUMMARY OF THE INVENTION

The present invention is directed toward a method of making an orthodontic appliance preform and comprises the steps of moving a web having a textured portion toward a cavity of orthodontic appliance preform forming tooling, and introducing a quantity of molding material into the cavity for making a preform of the orthodontic appliance. The method also includes the steps of forming the preform with the molding material in the cavity while a portion of the molding material is in contact with the textured portion of the web, and degrading the textured portion of the web to remove the textured portion and thereby impart a textured surface on the preform.

Use of a web offers significant advantages in the method of making the orthodontic appliance. As one advantage, the textured portion of the web when pressed to a sufficient depth into the molding material provides undercut regions on the preform once the textured portion is removed. As another advantage, the web may optionally serve as a transport device to convey the preform away from the forming tooling at an appropriate time. The shape or pattern of the textured portion of the web can be chosen to provide a witness impression on the preform that resembles in substantial part the appearance of a conventional orthodontic bracket having a mesh base.

BRIEF DESCRIPTION OF THE DRAWINGS

FIG. 2 is an inverted, perspective view of a former used with a method in accordance with another embodiment of the invention;

FIG. 3 is an exploded, schematic, perspective view of forming tooling (including the former shown in FIG. 2) that is somewhat different from the forming tooling shown in FIG. 1;

FIG. 4 is a side cross-sectional view of the forming tooling illustrated in FIG. 3, shown in assembled relation;

FIG. 5 is a reduced top schematic view of a method of making an orthodontic appliance according to another embodiment of the invention; and FIG. 6 is a fragmentary, side cross-sectional view of a die cutting station used with the method shown in FIG. 1.

DETAILED DESCRIPTION OF THE PREFERRED EMBODIMENTS

Figure 1:
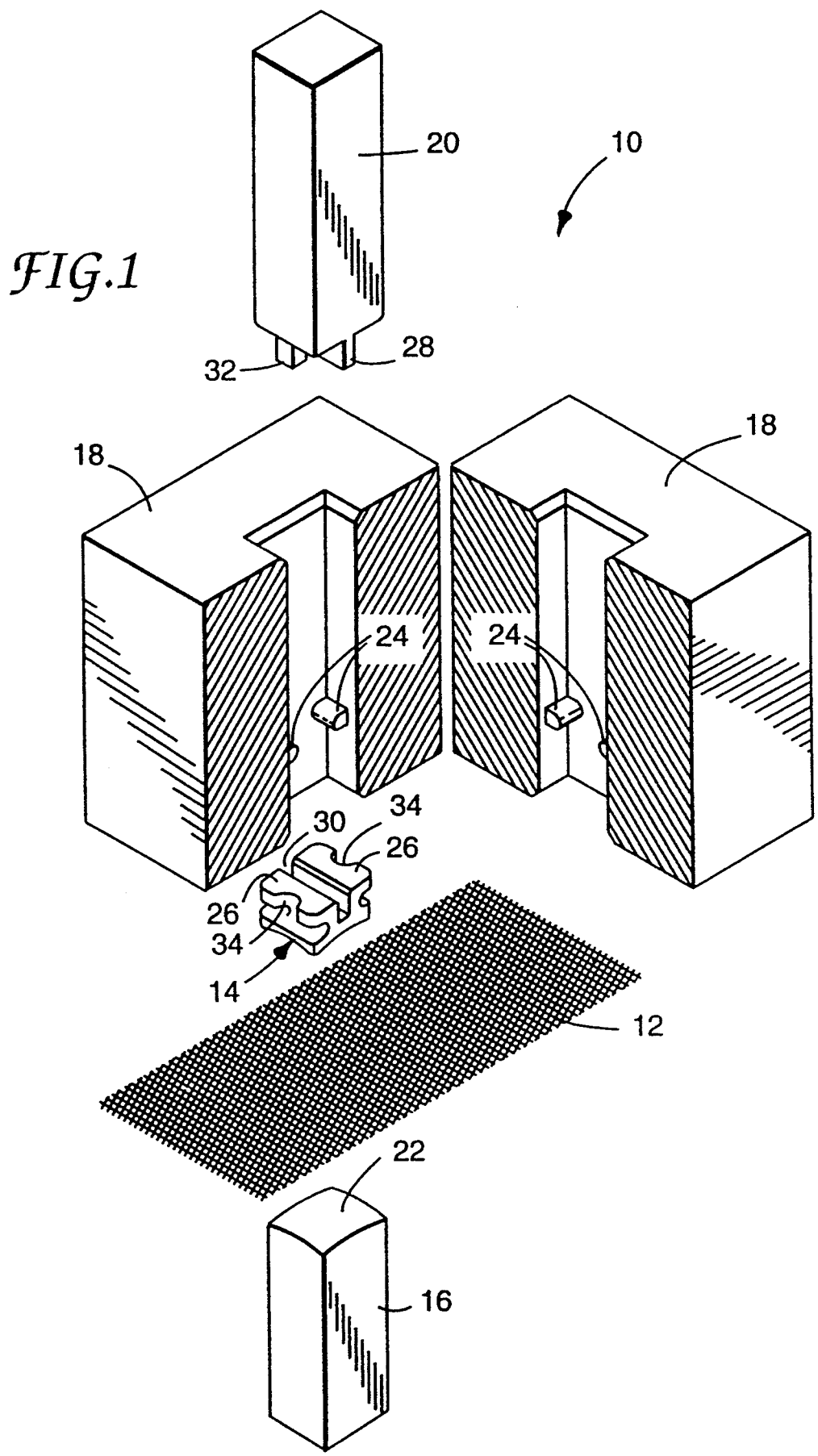
FIG. 1 is an exploded, schematic perspective illustration of a method of making an orthodontic appliance according to the present invention.

Referring initially to FIG. 1, forming tooling, broadly designated by the numeral 10, is shown in exploded format and is used in conjunction with a web 12 for making an orthodontic appliance preform such as an orthodontic bracket preform 14 according to the method of the present invention. The forming tooling 10 includes a base former 16, mesial and distal mold sections 18 and a buccal or labial surface former 20.

The base former 16 includes a convex upper surface 22 having a compound contour that matches the shape of the tooth surface to which the bracket 14 is to be bonded. The base former 16 fits within a vertical cavity that is formed when the mesial and distal mold sections 18 are brought together toward a closed, abutting orientation. The mesial and distal mold sections 18 are shown in FIG. 1 in an orientation 90 degrees apart from one another for illustrative purposes so that the interior of each mold section 18 can be observed in the drawing; in practice, however, the sections 18 are located 180 degrees apart from each other and are moved in straight-line fashion toward or away from each other by hydraulic piston and cylinder assemblies when desired to close or open the vertical cavity in connection with a forming operation.

Each of the mesial and distal mold sections 18 includes an opposed pair of tiewing undercut formers 24 that serve to form a ligature groove beneath the four tiewing portions 26 of the bracket preform 14. The mesial and distal mold sections 18 also have walls that form the mesial and distal sides of the bracket preform 14, as well as occlusal and gingival sections adjacent the ligature grooves.

The buccal-labial former 20 includes a mesiodistally-extending section 28 for forming an archwire slot 30 of the bracket preform 14. In addition, the buccal-labial former 20 includes a pair of centrally located projections 32 located on either side of the section 28, for forming occlusal and gingival positioning notches 34 on the bracket preform 14 between respective pairs of tiewing portions 26. Remaining downwardly facing surfaces of the buccal-labial former 20 form the outer buccal or labial surface of the bracket preform 14. The base former 16 and the buccal-labial former 20 are connected to opposing rams of a hydraulic press that is computer controlled to precisely control both the motion and the stroke length of the rams.

The web 12 has a textured portion, and preferably is entirely textured as shown in the drawings. The textured portion preferably includes a series of spaced apart openings, and more preferably is a woven mesh made of a polymeric material such as polypropylene. The mesh preferably is made of fibers having a cross pattern of a size that is effective for use with a selected adhesive. Generally speaking, the mesh cross pattern should have a size equivalent to 80 mesh or smaller.

In accordance with the method of the present invention, the mesial and distal mold sections 18 are brought together to a closed position such that the vertical forming cavity is established. The base former 16 is advanced by the press in an upward direction and comes in contact with the web 12 that extends horizontally directly beneath the vertical forming cavity. Further advancement of the base former 16 in an upward direction moves the upper portion of the base former 16 with the engaged portion of the web 12 slightly into the bottom of the forming cavity. The tension on the web 12 is controlled by the computer mentioned above, and is relaxed somewhat as the base former 16 ascends in order to enable the engaged portion of the web 12 to ascend with the base former 16 into the bottom of the forming cavity.

Next, a measured quantity of molding material is introduced into the forming cavity. The buccal-labial former 20 then descends into the vertical forming cavity, and the base former 16 resumes vertical ascent as necessary. If desired, the tooling 10 (such as by a heating jacket surrounding the mold sections 18) and the molding material may be preheated to enhance the flow characteristics of the molding material. Next, sufficient pressure is directed to the base former 16 and the buccal-labial former 20 by the hydraulic press such that air space in the forming cavity is eliminated and the molding material is formed into the preform 14.

As the molding material is shaped into the preform 14 in the forming cavity, a portion of the molding material is in contact with and is preferably embedded into the textured portion of the web 12 that is above the upper surface 22 of the base former 16. Once the preform 14 is pressed into the approximate shape of an orthodontic bracket, the forming tooling 10 is opened by lifting the buccal-labial former 20, moving the mesial and distal mold sections 18 horizontally away from one another, and lowering the base former 16, whereupon the preform 14 remains, supported on the web 12.

The web 12 is then advanced along its length to move the preform 14 in a horizontal direction away from the forming tooling 10, and to a die cutting station as shown in FIG. 6. At the die cutting station, the base of the preform 14 is supported by a post 35 while a die 37 descends over the preform 14 to cut the web 12 around the periphery of the base of the preform 14. The cutting edge of the die 37 in FIG. 6 is constructed to closely match the shape of the preform base. Alternatively, however, a somewhat larger circular punch (similar to a gasket punch) is employed so that a single punch may be used with a variety of preform configurations, inasmuch as the excess web material will subsequently volatilize in the oven during the steps described below.

Next, the preform 14 with its attached cut portion of the web is grasped by a robotic arm and placed on a dewaxing tray. When a sufficient number of preforms 14 are placed on the tray, the tray is moved into an oven where the preform 14 with its attached cut portion of the web is subjected to heat. As the temperature of the cut portion of the web rises, the cut portion of the web pyrolytically degrades to fugative volatile components, whereupon an undercut witness of the web is left in the base of the preform 14.

The molding material is preferably made of a 300 series, 400 series, or 17-4 PH stainless steel powder that is mixed with a binder material as well as flow enhancing agents useful in making small sintered metal parts with intricate shapes. Preferably, the web 12 is made of polypropylene which is also a major component or backbone of the binder material. As a result, as the web 12 is volatilized in the oven, the binder material also volatilizes (or at least partially volatilizes) so that the preform 14 is ready for sintering.

Optionally, thermal degradation of the web 12 and debinding of the preform 14 are carried out in a hydrogen atmosphere, where the fugitive polypropylene thermally decomposes to form methane and other hydrocarbons. Monitoring of the methane levels in the oven provides a status indication of the completeness of the debinding operation, and the preform 14 can be removed from the oven as soon as the methane level drops below a certain value.

Waxes are commonly used as flow agents for sintered metal processing, so that the metal powder readily flows into all areas of the mold during the forming operation. The wax is removed before the debinding operation by slowly heating the preform over a period of time so as to volatilize the wax without volatilizing the binder. The binder functions to hold the preform together once the wax is removed and until such time as the sintering operation is completed.

As an alternative, the web 12 is made of a material that volatilizes at a temperature lower than the volatilization temperature of the binder material. As an example, both the web 12 and the flow enhancing agents can be made of waxes having a relatively low melting or softening temperature, while the binder material has a relatively high melting or softening temperature. The flow enhancing agents and the web are removed before the debinding operation by slowly heating the preform over a period of time so as to burn off the wax without burning off the binder.

Preferably, the molding material is precisely measured to a certain volume quantity and is initially shaped to the form of a spheroid for convenient handling. The spheroid is introduced into the vertical cavity of the forming tooling 10 by a tube or other means at the proper time. Optionally, the spheroid is preheated by passing the spheroid through a tube that is made of a ceramic material and that is subjected to an induction heater. Introduction of the molding material, closing, pressing and opening of the forming tooling 10, and advancement of the web 12 are preferably controlled by the computer controlling movement of the hydraulic press and tension of the web 12 such that automatic operation is provided.

Once the waxes or other flow-aiding agents, the binder material and the textured portion of the web 12 have volatilized, the temperature in the oven is raised to a higher temperature at which the metal powder sinters and the preforms are made into orthodontic appliances. The appliances are then tumbled, cleaned and electro-polished. The time and temperature cycles of the oven are also controlled by the computer.

The method for making an orthodontic appliance according to the invention as illustrated by the schematic drawing in FIGS. 2-4 is somewhat similar to the method illustrated in FIG. 1, except that the embodiment shown in FIGS. 2-4 includes the use of forming tooling 110 that is somewhat different than the forming tooling 10 shown in FIG. 1. The forming tooling 110 includes a rectangular bushing 117 and four slidable carbide core pulls designated as tiewing undercut formers 119 that are movable through tiewing undercut former channels 121 provided on opposite sides of the bushing 117.

The forming tooling 110 includes a base former 116 having an upper surface 122 somewhat similar to the upper surface 22 illustrated in FIG. 1. However, the base former 116 also includes lateral extensions 123 that project in occlusal and gingival directions and contact the underside of the tiewing undercut formers 119 when the forming tooling 110 is closed.

The forming tooling 110 includes a buccal-labial former 120 having a pair of elongated, rectangular sections 128 for forming an archwire slot, and having an opposed pair of projections 132 for forming a vertical channel between tiewings of the twin-shaped preform. The buccal-labial former 120 also includes lateral extensions 125 that contact the upper surface of the four tiewing undercut formers 119 when the forming tooling 110 is closed. FIG. 4 illustrates the forming tooling 110 in its closed position for forming a preform.

The embodiment depicted in FIG. 5 illustrates a method of using the forming tooling 110 to make an orthodontic appliance that is somewhat different from the methods described above. In FIG. 5, a rotary table 200 is provided, and a bushing 117 is positioned near the circumference of the table 200. The bushing 117 is advanced in sequence to the station marked "A" where the rotary table 200 stops, the tiewing undercut formers 119 located in outer portions of respective channels in the bushing 117 are moved inwardly into the vertical forming cavity, and the base former 116 is advanced upwardly toward the vertical forming cavity.

As the base former 116 ascends, the upper surface of the base former 116 contacts a portion of a web 212 that is advanced by a computer-controlled indexing device 213. As the base former 116 continues to ascend into the bushing 117, a peripheral edge of the base former 116 contacts a rectangular-shaped inner cutting edge of the bushing 117 such that a rectangular portion of the web 212 within the cutting edge is severed from remaining portions of the web. The web portion is then trimmed along the periphery of the upper surface 122 as the latter passes by the inside, lower edge of the four tiewing undercut formers 119. (Remaining web trimmings are removed later by pressurized air, as described below.) The rotary table 200 is then moved to advance the bushing 117, the base former 116 and the cut portion of the web to the station marked "B".

At station "B", a measured volume quantity of molding material is introduced into the vertical cavity of the bushing 117. Next, the table 200 is moved to direct the bushing 117 to the station marked "C" where the buccal-labial former 120 descends into the vertical cavity of the bushing 117. The table 200 is then advanced to move the assembly of the forming tooling 110, the cut web portion and the molding material to the station marked "D" in FIG. 4, whereupon the assembly is heated to a temperature in the range of 40° C. to 200° C. to enhance the flow characteristics of the molding material.

Next, the table 200 is advanced to move the assembly to the station marked "E", where the base former 116 and the buccal-labial former 120 engage rams of a hydraulic press and are moved toward each other by the rams a precise distance under sufficient pressure to mold a preform. The rams then retract and disengage the formers 116, 120 and the assembly is advanced by the table 200 to the station marked "F" where the buccal-labial former 120 is lifted from the forming cavity of the bushing 117. Next, the table 200 moves the assembly to the station marked "G" where the four tiewing undercut formers 119 are retracted from the vertical forming cavity of the bushing 117 (without detaching from the bushing 117). The table 200 is then indexed to move the bushing 117 to the station marked "H", where the base former 116 is raised to move the preform through the bushing cavity until the preform is above and clear of the bushing 117.

Next, a robotic arm 215 grasps the preform at the station "H" above the bushing 117 and moves the preform through an arc of 180 degrees toward a rotary dewaxing tray 231. Subsequently, a blast of pressurized air is directed to the tooling 110, and the air stream removes any remaining cut-off web trimmings from the lateral extensions 123 of the base former 116. The tray 231 then turns in indexed fashion in preparation to receive each preform, so that the preforms are placed in somewhat different angular locations on the tray 231 relative to its rotational axis. In addition, the arm 215 is controlled for movement toward or away from the center of the dewaxing tray 231, such that a helical pattern of preforms is made on the tray 231 to assist in maximizing the number of preforms placed on the tray 231.

Once the dewaxing tray 231 is loaded with preforms, the tray 231 is placed in an oven for dewaxing, debinding and sintering the preforms. The resultant orthodontic appliances have a base with a witness impression of the patterned web.

While the foregoing process has been described in connection with orthodontic appliances made of sintered metal, it should be understood that the method is also useful for making non-metallic orthodontic appliances made of materials such as ceramics or plastics, so long as the step of degrading the textured portion of the web does not adversely affect the preform. For example, if the web is degraded by heat, the temperature of decomposition of the web should be lower than the temperature of decomposition of the molding material.

Plastic molding material could include fiber reinforcement such as described in assignee's copending U.S. patent application Ser. No. 07/903,568, now U.S. Pat. No. 53,184,440, filed Jun. 24, 1992, the disclosure of which is expressly incorporated into the present disclosure. Ceramic molding materials could include the materials described in U.S. Pat. No. 4,954,080 which is also expressly incorporated by reference herein.

In addition, while the foregoing detailed description exemplifies a method of press molding an orthodontic appliance, the method is also useful for injection molding of orthodontic appliances. Injection molding may be carried out using a split mold that is opened to place web portions in the mold cavity.

Moreover, while a heating operation has been described as useful for degrading the web to leave an undercut witness on the preform, other methods might be equally beneficial. For example, the web may be made of a material that is degradable in water or other solvents, such that soaking the preform in the solvent dissolves the web material to leave the textured impression. (In such a method, however, a solvent must be selected that does not adversely affect the preform.) Accordingly, the term "degrading" should not be limited to thermal degradation, but instead should be considered as any process that breaks down the web or partially breaks down the web into its component parts or otherwise changes its physical properties (such as its strength).

As another alternative, the step of degrading the web, need not be carried out by completely degrading or completely decomposing the web. As an example, the plastic web may be heated only to a temperature at which the web is softened and can be easily pulled away in one piece fashion from the base of the preform without disturbing the textured impression.

As another alternative, the preform may be formed in part before coming into contact with the textured portion of the web. For example, the mold assembly may be closed to form tiewings, ligature grooves and/or ligature notches and then partially opened by lowering the base former. Next, the web is moved under the vertical forming cavity, and the base former is again raised to press the web against the partially formed preform as desired.

In some instances, it may be possible to degrade the web at the same time that the preform is changed into an orthodontic appliance. For example, the web may be volatilized at the same time that the preform is sintered into an appliance. In such instances, the terms "preform" and "appliance" shall be deemed equivalent as appropriate, for the purpose of interpreting the following claims.

We claim:

1. A method of making an orthodontic appliance preform comprising the steps of:
   moving a web having a textured portion toward a cavity of orthodontic appliance preform forming tooling;
   introducing a quantity of molding material into the cavity of the tooling;
   forming the preform with the molding material in the cavity while a portion of the molding material is in contact with the textured portion of the web; and
   degrading the textured portion of the web to remove the textured portion and thereby impart a textured surface on the preform.

2. The method of claim 1, including the step of moving the preform away from the cavity before said step of degrading the textured portion of the web.

3. The method of claim 1, wherein the textured portion of the web includes apertures, whereby said step of degrading the textured portion of the web exposes undercuts on the textured surface of the preform.

4. The method of claim 3, wherein said web is a mesh made of polymeric material.

5. The method of claim 1, wherein the molding material includes a binder, and wherein said step of degrading the textured portion of the web includes the step of heating the preform to thermally degrade the textured portion of the web and to debind the preform.

6. The method of claim 5, wherein the molding material includes a curable polymer, and wherein said step of heating the preform includes the step of curing the polymer.

7. The method of claim 1, wherein said step of forming the preform includes a first step of forming tiewing portions and an archwire slot of the preform and a second step of forming a textured base surface by contacting the molding material with the textured portion of the web.

8. The method of claim 1, wherein said step of forming the preform includes the step of press molding or injection molding the preform.

9. The method of claim 1, including the step of cutting the portion of the web in contact with the preform from remaining portions of the web before said step of heating the preform to thermally degrade the textured portion of the web.

10. The method of claim 1, wherein said step of forming a preform of the appliance includes the step of moving one or more core pulls in the cavity to make grooves, slots or other shapes in the preform.

11. The method of claim 1 including the steps of cutting the web into a plurality of textured portions each contacting a respective preform, and placing the cut portions of the web with the preforms onto a tray for heating.

12. The method of claim 1, wherein said step of forming the preform includes the step of partially forming the preform before the molding material is in contact with the textured portion of the web.

13. The method of claim 1, wherein said step of degrading the textured portion of the web includes the step of volatilizing the textured portion of the web.

14. The method of claim 1, wherein said step of degrading the textured portion of the web includes the step of dissolving the textured portion of the web.

15. The method of claim 1, wherein said step of degrading the textured portion of the web includes the step of softening the textured portion of the web.

16. The method of claim 1, wherein said step of moving the web includes the step of moving the web adjacent a rotary table carrying at least a portion of the forming tooling.

17. The method of claim 1, including the step of cutting the web as the forming tooling is closed to form the preform.

* * * * *